United States Patent
Simpson et al.

(10) Patent No.: US 6,648,875 B2
(45) Date of Patent: Nov. 18, 2003

(54) MEANS FOR MAINTAINING TENSION ON A STEERING TENDON IN A STEERABLE CATHETER (75) Inventors: John A. Simpson, Carlsbad, CA (US); Robert C. Hayzelden, Canyon Lake, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/849,325

(22) Filed: May 4, 2001

(65) Prior Publication Data
US 2002/0165485 A1 Nov. 7, 2002

(51) Int. Cl.[7] ..................... A61M 25/098; A61M 25/00; A61B 5/00
(52) U.S. Cl. .......................... 604/528; 600/585
(58) Field of Search ................. 604/528, 523; 600/433, 434, 435, 585

(56) References Cited

U.S. PATENT DOCUMENTS

| | | |
|---|---|---|
| 3,071,161 A | 1/1963 | Ulrich |
| 3,253,524 A | 5/1966 | Ashizawa et al. |
| 3,521,620 A | 7/1970 | Cook |
| 3,572,325 A | 3/1971 | Bazell et al. |
| 3,897,775 A | 8/1975 | Furihata |
| 4,483,326 A | 11/1984 | Yamaka et al. |
| 4,557,254 A | 12/1985 | Yamaguchi |
| 4,586,923 A | 5/1986 | Gould et al. |
| 4,841,950 A | 6/1989 | Fukuda |
| 4,921,482 A | 5/1990 | Hammerslag et al. |
| 4,998,916 A | 3/1991 | Hammerslag et al. |
| 5,037,391 A | 8/1991 | Hammerslag et al. |
| 5,108,368 A | 4/1992 | Hammerslag et al. |
| 5,195,968 A | 3/1993 | Lundquist et al. |
| 5,199,950 A | 4/1993 | Schmitt et al. |
| 5,228,441 A | 7/1993 | Lundquist |
| 5,254,088 A | 10/1993 | Lundquist et al. |
| 5,273,535 A | 12/1993 | Edwards et al. |
| 5,299,562 A | 4/1994 | Heckele et al. |
| 5,315,996 A | 5/1994 | Lundquist |
| 5,318,525 A | 6/1994 | West et al. |
| 5,318,526 A | 6/1994 | Cohen |
| 5,322,064 A | 6/1994 | Lundquist |
| 5,327,905 A | 7/1994 | Avitall |
| 5,329,923 A | 7/1994 | Lundquist |
| 5,334,145 A | 8/1994 | Lundquist et al. |
| 5,336,182 A | 8/1994 | Lundquist et al. |
| 5,358,478 A | 10/1994 | Thompson et al. |
| 5,363,861 A | 11/1994 | Edwards et al. |

(List continued on next page.)

FOREIGN PATENT DOCUMENTS

WO    WO 00/06242    2/2000

OTHER PUBLICATIONS

Grafton A. Smith, M.D. and Edwin L. Brackney, M.D., "Preliminary Report on a New Method of Intestinal Intubation with the Aid of a Flexible Stylet with Controllable Tip," Dept. of Surgery, University of Minnesota Medical School, vol. 27, #6, Jun. 1950, pp. 817–821.

*Primary Examiner*—Manuel Mendez
*Assistant Examiner*—Mark K Han
(74) *Attorney, Agent, or Firm*—Fulwider Patton Lee & Utecht, LLP (57) ABSTRACT

A catheter handle includes a steering controller to be used in conjunction with a steerable catheter shaft, and a steering tendon tensioning device. The operator deflects the profile of a distal-end region of the catheter by rotating the steering controller. Spring devices located on the steering tendons maintain the steering tendons in tension during manipulation of the steering controller. A locking device locks the steering controller in place relative to the handle.

25 Claims, 6 Drawing Sheets

U.S. PATENT DOCUMENTS

| | | |
|---|---|---|
| 5,364,351 A | 11/1994 | Heinzelman et al. |
| 5,383,852 A | 1/1995 | Stevens-Wright |
| 5,383,923 A | 1/1995 | Webster, Jr. |
| 5,395,327 A | 3/1995 | Lundquist et al. |
| 5,456,664 A | 10/1995 | Heinzelman et al. |
| 5,465,716 A | 11/1995 | Avitall |
| 5,471,982 A | 12/1995 | Edwards et al. |
| 5,478,330 A | 12/1995 | Imran et al. |
| 5,507,725 A | 4/1996 | Savage et al. |
| 5,512,035 A | 4/1996 | Konstorum et al. |
| 5,531,686 A | 7/1996 | Lundquist et al. |
| 5,545,200 A | 8/1996 | West et al. |
| 5,642,736 A | 7/1997 | Avitall |
| 5,687,723 A | 11/1997 | Avitall |
| 5,728,144 A | 3/1998 | Edwards et al. |
| 5,755,760 A | 5/1998 | Maguire et al. |
| 5,762,067 A | 6/1998 | Dunham et al. |
| 5,810,802 A | 9/1998 | Panescu et al. |
| 5,820,591 A | 10/1998 | Thompson et al. |
| 5,855,552 A | 1/1999 | Houser et al. |
| 5,860,953 A | 1/1999 | Snoke et al. |
| 5,865,800 A | 2/1999 | Mirarchi et al. |
| 5,891,088 A | 4/1999 | Thompson et al. |
| 5,893,885 A | 4/1999 | Webster, Jr. |
| 5,916,147 A | 6/1999 | Boury |
| 5,944,690 A | 8/1999 | Falwell et al. |
| 5,984,907 A | 11/1999 | McGee et al. |
| 5,987,344 A | 11/1999 | West |
| 6,007,531 A | 12/1999 | Snoke et al. |
| 6,017,322 A | 1/2000 | Snoke et al. |
| 6,022,343 A | 2/2000 | Johnson et al. |
| 6,027,473 A | 2/2000 | Ponzi |
| 6,033,378 A | 3/2000 | Lundquist et al. |
| 6,042,562 A | 3/2000 | Amor |
| 6,063,077 A | 5/2000 | Schaer |
| 6,132,390 A | 10/2000 | Cookston et al. |
| 6,142,994 A | 11/2000 | Swanson et al. |
| 6,163,716 A | 12/2000 | Edwards et al. |
| 6,208,881 B1 | 3/2001 | Champeau |

MEANS FOR MAINTAINING TENSION ON A STEERING TENDON IN A STEERABLE CATHETER

BACKGROUND OF THE INVENTION

The invention relates generally to a steerable catheter, and more particularly to a catheter handle having a steering controller for applying tension to a tendon to steer the catheter and a system for maintaining tension on the steering tendon when it is not tensioned by the steering controller.

In many medical procedures, it is necessary to place a catheter at a particular location within the patient's body. Precise placement of the catheter is more easily accomplished when a steerable catheter is used. Such catheters are typically flexible at the distal end, and the profile at the distal end is deflectable.

Changing the profile of the distal-end region of a steerable catheter typically involves the use of a steering tendon that is housed within the catheter shaft. The steering tendon is usually a wire that has its distal end attached to the distal-end region of the catheter shaft. The proximal end of the catheter shaft attaches to a handle. The proximal end of the steering tendon exits through the proximal end of the catheter shaft and attaches to a steering controller within the handle.

The profile of the distal-end region of the catheter shaft can be deflected from its non-steered configuration by manipulating the steering controller from a neutral position so that the steering tendon is axially displaced in the proximal direction. Axially displacing the steering tendon in the proximal direction places the steering tendon in tension which is reacted by offset and opposing compressive forces within the catheter shaft. These opposing tensile and compressive forces create a bending moment that acts upon the distal-end region of the catheter shaft, preferentially on the side where the steering tendon is attached, thereby deflecting the distal-end region. If the steering controller is released, the distal-end region of the catheter shaft typically springs back to its natural state due to the structure of the catheter shaft, thus moving the steering tendon and the steering controller back to their neutral positions.

It is often necessary to maintain the force exerted on the steering tendon during the course of a medical procedure so as to retain the deflected profile of the distal-end region of the catheter. In some of the existing steerable catheters, maintaining the force exerted on the steering tendon requires the operator to manually hold the steering controller in place. However, it is often difficult for the operator to maintain a constant amount of force on the steering tendon for an extended period of time or while further manipulating the handle.

In other existing steerable catheters, an additional knob attached to the steering controller is used to lock the displacement of the steering tendon at its present position. This knob is used to tighten the steering controller against a friction plate within the handle housing until the resulting friction is sufficient to prevent the steering controller from moving from its present position. Typically, the operator must turn this knob with one hand while the other hand is used to maintain the preferred position of the steering controller relative to the handle housing. Thus, locking the steering controller in other steerable catheters is a two-handed operation.

Steerable catheters that utilize steering tendons can have either single or multiple steering tendons. During the use of a multiple-tendon steerable catheter, manipulation of the steering controller results in the application of tension to one steering tendon, while no force is deliberately applied to any other tendon. Tendon wires in steerable catheters are typically small in diameter in order to conserve catheter lumen space. Tendon wires are usually made of a wire material possessing a high modulus of elasticity and high yield strength so that they exhibit minimal elastic stretch and will not permanently deform under ordinary tensile loads. However, because of their relatively small diameters, catheter tendon wires can be easily bent and are prone to buckling when subjected to axial compressive forces.

The majority of a tendon wire's length is typically protected from bending by virtue of the inherent rigidity of the surrounding catheter shaft. Further, buckling of a tendon wire within the catheter shaft is unlikely because the tendon wire is typically supported by a dedicated tendon sheath or lumen, or at least by the wall of the main catheter lumen. However, within a catheter's handle, a tendon wire typically has an unsupported span between the proximal end of the catheter shaft and the steering linkage to which the tendon is attached. When subjected to repeated steering, this span may be susceptible to kinking, which can adversely affect the catheter's steering performance.

Figure 1A:
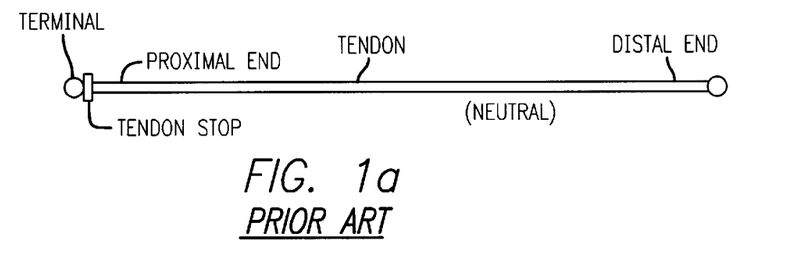
FIGS. 1a–1c are schematic diagrams of a prior art catheter steering system having a steering tendon passing through a stop, showing the tendon in a neutral (non-steered) position, a tensed (steered) state and a relaxed (non-steered) state.
Figure 1B:
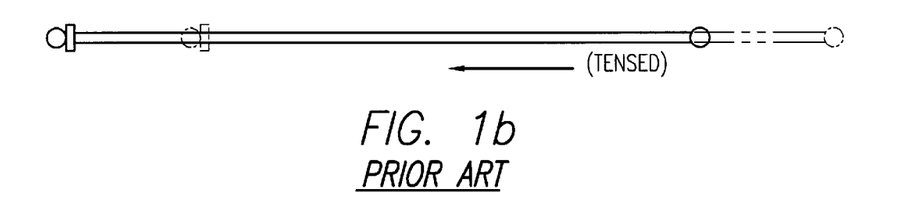
Figure 1C:
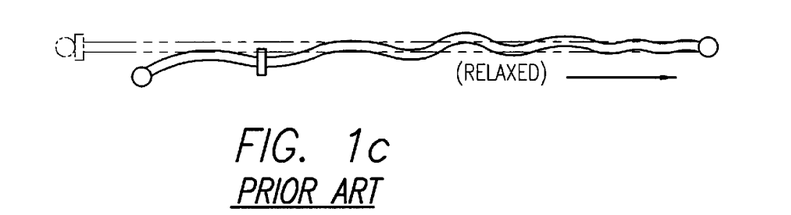

In some existing catheters, the proximal ends of all steering tendons are rigidly affixed to their respective linkage points. As a result, when tension is applied to only one tendon, the other tendons may be forced to bow or kink in response to the catheter shaft's unavoidable length change. Other steerable catheters attempt to avoid that problem by routing each steering tendon through a hollow stop within the handle's steering linkage system and affixing a terminal to the proximal end of each steering tendon. In that configuration (see FIG. 1a), all terminals typically butt against their respective stop when the catheter is in its neutral (non-steered) position. When tension is applied to only one steering tendon to steer the catheter (see FIG. 1b), the extraneous length in all other tendons can pass through their respective hollow stop. However, a corresponding gap between the hollow stop and the terminal then exists, resulting in a relaxed steering tendon that may be subject to bowing or kinking (see FIG. 1c).

Hence, those skilled in the art have identified a need for an improved steering system for steering a catheter, and one that reduces or minimizes the slack in steering tendons. The present invention fulfills these needs and others.

SUMMARY OF THE INVENTION

Briefly, and in general terms, the present invention is directed to a system in which a steering controller includes a device to maintain the steering tendon in tension when it is not tensioned by the steering controller.

In a first aspect, the invention relates to a system for applying tension to a steering tendon. The tendon has a distal end that is attached to the distal-end region of a catheter shaft and a proximal end that exits the proximal end of the shaft. The system also includes a movable steering controller and means for coupling the tendon to the steering controller. Through the coupling means, movement of the controller in a first direction relative a neutral position increases tension on the tendon and movement of the controller in a second direction relative the neutral position, and opposite the first direction, maintains tension on the tendon.

In a detailed aspect of the invention, the coupling means includes a stop that is disposed at the controller and has the proximal end of the tendon passing therethrough and terminating at a point that is a distance from the stop, and a spring device that has a distal end at the stop and a proximal end attached to the tendon at a location proximal to the stop. In a more detailed aspect, the spring device is in a fully compressed state when the steering controller is in the neutral position and when the steering controller is moved in the first direction. In a further aspect, the spring device is in a partially compressed state when the steering controller is in the neutral position, and the compression increases when the steering controller is moved in the first direction. In another detailed aspect, the spring device extends in length, yet remains in compression, when the steering controller is moved in the second direction. In another detailed aspect, the spring device includes a wire coil that surrounds the tendon between the stop and the proximal end of the tendon. In yet another detailed aspect, the catheter shaft has an inherent bending stiffness and the tension imparted by the coupling means when the controller is in the neutral position has negligible impact on the profile of the catheter shaft.

In a second aspect, the invention relates to a system for steering a catheter shaft. The catheter shaft has a proximal region and a distal-end region and at least one steering tendon that has a distal end attached to the shaft distal-end region and a proximal end that exits the shaft proximal end. The system includes a steering controller. The proximal end of the at least one steering tendon is coupled to the steering controller in such a manner that when the controller is in a neutral position, tension is applied to the tendon. The system also includes means for increasing tension on the tendon when the controller is moved in a first direction away from the neutral position. The system further includes means for maintaining tension on the tendon when the controller is moved from its neutral position in a second direction opposite the first direction.

In a detailed aspect, the means for increasing tension on the tendon includes a spring device that is coupled to the controller at one end, secured to the tendon at the other end, and is adapted to be substantially in a fully compressed state when the controller is moved in the first direction. In another aspect, the means for maintaining tension on the tendon includes a spring device that is coupled to the controller at one end, secured to the tendon at the other end, and is adapted to extend in length, yet remain in compression, when the controller is moved in the second direction.

In a third aspect, the invention relates to a system for steering a catheter shaft. The catheter shaft has a proximal region and a distal-end region and at least one steering tendon that has a distal end attached to the shaft distal-end region and a proximal end that exits the shaft proximal end. The system includes a controller that has the proximal end of the at least one steering tendon coupled thereto and is adapted to move the proximal end of the tendon. The system also includes a spring device that is coupled between the proximal end of the tendon and the controller. The spring device is configured to maintain tension on the tendon. Movement of the controller in a first direction relative to a neutral position increases the tension on the tendon.

In a detailed aspect of the invention, the spring device is secured at one end to the proximal end of the tendon and at the other end to the controller and the spring device is configured to be fully compressed during controller movement in the first direction. In another aspect, the spring device is secured at one end to the proximal end of the tendon and at the other end to the controller and the spring device is configured to extend in length, yet remain in compression, during controller movement in a second direction relative to the neutral position and opposite the first direction. In yet another aspect, the spring device includes any one of a compression spring, tension spring, and leaf spring.

In a fourth aspect, the invention relates to a system for applying tension to a first steering tendon and a second steering tendon. Each tendon has a distal end that is attached to the distal-end region of a catheter shaft and a proximal end that exits the proximal end of the shaft. The system includes a movable steering controller and means for coupling the first and second tendons to the steering controller. Through the coupling means, movement of the controller in a first direction relative a neutral position increases tension on the first tendon while maintaining tension on the second tendon. Also through the coupling means, movement of the controller in a second direction relative the neutral position increases tension on the second tendon while maintaining tension on the first tendon.

In a detailed aspect, the coupling means includes a first stop that is disposed at the controller and has the proximal end of the first tendon passing therethrough and terminating at a point a distance from the first stop, a first spring device that has a distal end at the first stop and a proximal end attached to the proximal end of the first tendon, a second stop that is disposed at the controller and has the proximal end of the second tendon passing therethrough and terminating at a point a distance from the second stop, and a second spring device that has a distal end at the second stop and a proximal end attached to the proximal end of the second tendon. In a more detailed aspect, the first and second spring devices are in a compressed state when the steering controller is in the neutral position and thereby maintain tension on the first and second tendons respectively. In an even more detailed aspect, the catheter shaft has an inherent bending stiffness and the tension imparted by the first and second spring devices when the controller is in the neutral position has negligible impact on the profile of the catheter shaft. In another aspect, the first spring device is in a fully compressed state and the second spring device has extended, yet remains in a compressed state when the controller is moved in the first direction, and the second spring device is in a fully compressed state and the first spring device has extended, yet remains in a compressed state when the controller is moved in the second direction. In a further aspect, the first and second spring devices are in a partially compressed state when the steering controller is in the neutral position, but the compression increases on the first spring device then the steering controller in moved in a first direction and the compression increases on the second spring device when the steering controller is moved in a second direction.

In a fifth aspect, the invention relates to a handle for steering a catheter shaft. The catheter shaft has a proximal region and a distal-end region and at least one steering tendon. The steering tendon has a distal end that is attached to the shaft distal-end region and a proximal end that exits the shaft proximal end. The handle includes a housing that is attached to the proximal end of the catheter shaft. The handle also includes a movable steering controller that is connected to the housing. The handle further includes means for locking the steering controller in place relative to the shell housing. Also included in the handle is means for moving the steering controller from the locked position to a free position. Moreover, the handle includes means for coupling the tendon to the steering controller. Movement of the controller in a first direction relative a neutral position increases tension on the tendon and movement of the controller in a second direction relative the neutral position, and opposite the first direction, maintains tension on the tendon.

In a sixth aspect, the invention relates to a catheter. The catheter includes a catheter shaft that has a proximal region and a distal-end region. The catheter shaft also includes at least one steering tendon that has a distal end attached to the shaft distal-end region and a proximal end that exits the shaft proximal end. The catheter also includes a handle for steering the catheter shaft. The proximal end of the shaft is attached to the handle. The handle includes a housing that has a plurality of alternating protrusions and recesses. The catheter further includes a steering controller that is carried by the handle. The steering controller has a plurality of alternating protrusions and recesses. The proximal end of the steering tendon is connected to the steering controller and the steering controller is adapted to move the proximal end of the tendon. The catheter also includes a spring device that is coupled between the proximal end of the at least one tendon and the controller. The spring device is configured to maintain tension on the tendon. The steering controller is adapted to translate between a locked-position wherein at least one of the steering controller protrusions or recesses is interrelated with at least one of the housing protrusions or recesses, and a free-position wherein none of the steering controller protrusions or recesses is interrelated with any of the housing protrusions or recesses. Movement of the controller in a first direction relative to a neutral position increases the tension on the tendon.

These and other aspects and advantages of the invention will become apparent from the following detailed description and the accompanying drawings, which illustrate by way of example the features of the invention.

BRIEF DESCRIPTION OF THE DRAWINGS

FIG. 8a schematically shows both tendons while FIGS. 8b and 8c show separate tendons.

DETAILED DESCRIPTION OF THE PREFERRED EMBODIMENTS

Figure 2:
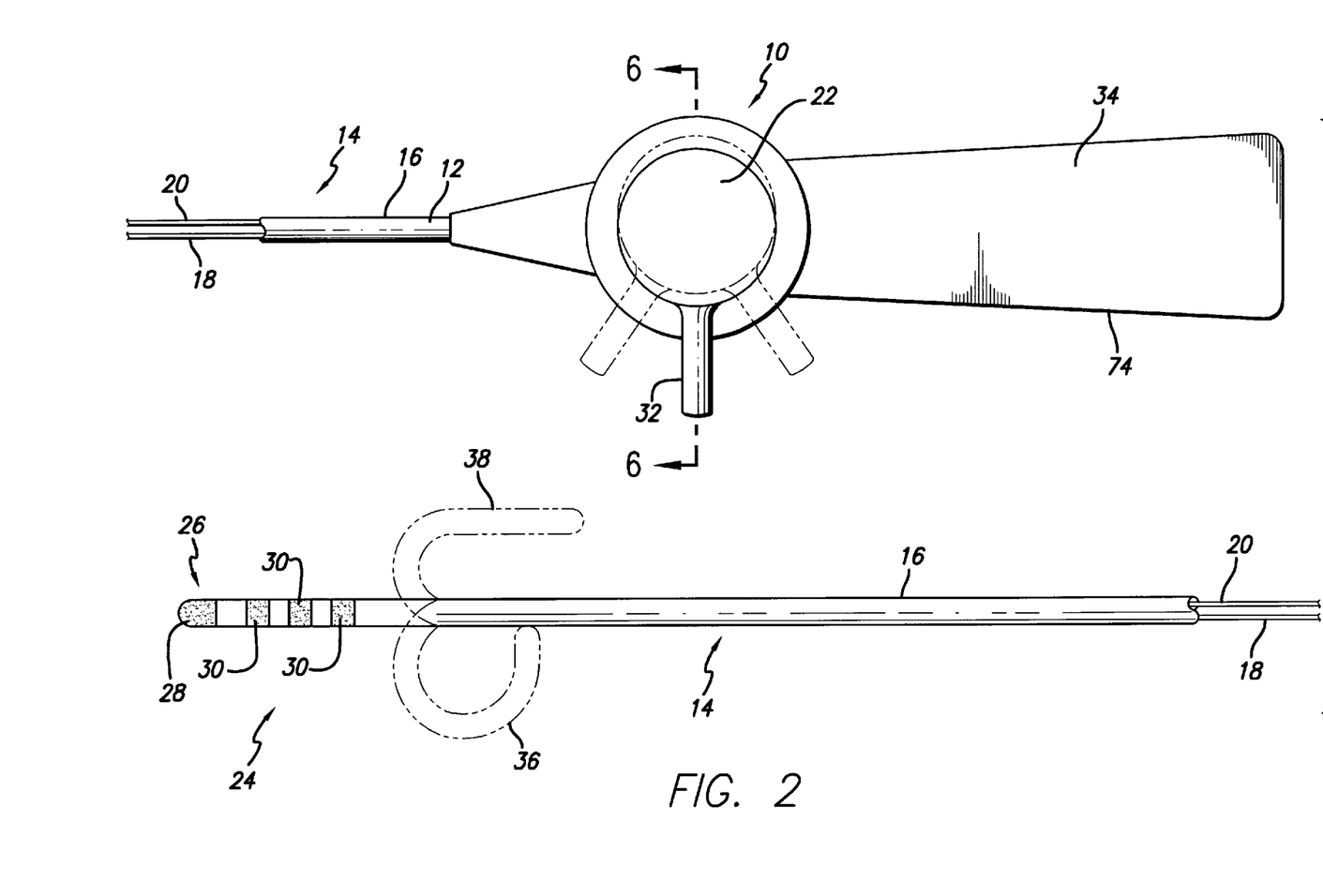
FIG. 2 is a plan view of a catheter handle and catheter configured in accordance with the invention and depicting major components of the catheter handle and catheter including a handle shell, a steering controller, and a catheter shaft.

Referring now to the drawings, in which like reference numerals are used to designate like or corresponding elements among the several figures, in FIG. 2 there is shown a catheter handle 10 for a steerable catheter incorporating aspects of the present invention. The catheter handle 10 attaches to a proximal end 12 of a catheter shaft 14. The catheter shaft 14 comprises a catheter sheath 16, a first steering tendon 18 and a second steering tendon 20. The first steering tendon 18 and the second steering tendon 20 exit from the proximal end of the catheter sheath 16 and enter the catheter handle 10. Within the catheter handle 10, the first 18 and second 20 steering tendons attach to a steering controller 22. The distal ends of the steering tendons 18, 20 are attached to a distal-end region 24 of the catheter, in a manner such as that disclosed in co-pending patent application having docket number HRT-55403, entitled "Dual-Profile Steerable Catheter with Shaft Support System for Resisting Axial Compressive Loads," that was filed on May 2, 2001, which is assigned to the assignee of the present invention and is hereby incorporated by reference.

With continued reference to FIG. 2, the distal-end region 24 of the catheter shaft 14 also includes an energy transfer device 26. In one configuration, the energy transfer device 26 includes a tip electrode 28 for applying ablation energy to a biological site. Proximal from the tip electrode 28 is a plurality of band electrodes 30 arranged in a substantially linear array along the distal-end region 24 of the sheath 16. The energy transfer device 26 includes individual lead wires (not shown) running from the catheter handle 10 to each band electrode 30. The lead wires are attached to the band electrodes 30, such as by welding. The energy transfer device 26 also includes a pair of thermocouple wires (not shown) running from the catheter handle 10 through the catheter sheath 16 to the tip electrode 28. The thermocouple wires are attached to the tip electrode 28, such as by soldering. One of the thermocouple wires also functions as a drive wire to transmit ablation energy to the tip electrode 28.

With further reference to FIG. 2, the profile of the distal-end region 24 of the catheter shaft 14 can be adjustably deflected by rotating the steering controller 22. A knob 32 portion of the steering controller 22 resides partially outside the handle's shell 34. The steering controller 22 can be rotated by rotating the knob 32 either in a first direction (clockwise) or in a second direction (counterclockwise). Rotating the knob 32 clockwise from a neutral position causes one of the steering tendons 18, 20 to translate axially in the proximal direction, thus creating a first changed profile 36 of the distal-end region 24 of the catheter shaft 14. Similarly, rotating the knob 32 counterclockwise from the neutral position causes the other steering tendon 18, 20 to translate axially in the proximal direction, thus creating a second changed profile 38 of the distal-end region 24 of the catheter shaft 14. Although FIG. 2 depicts the handle being used with a dual-profile catheter with two steering tendons 18, 20, the handle 10 is also functional for single-profile catheters with a single steering tendon.

Figure 3:
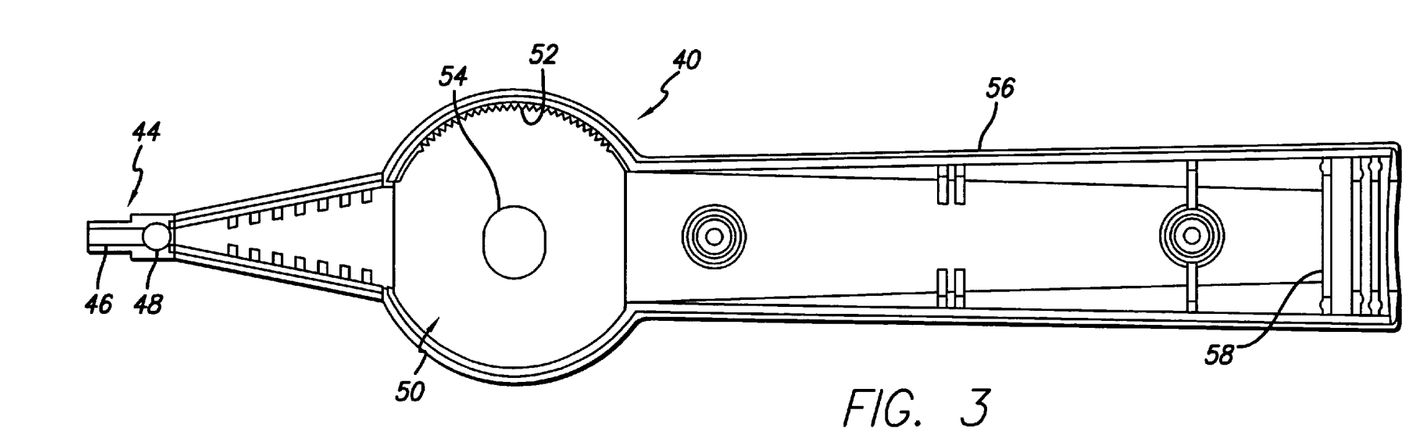
FIG. 3 is plan view depicting the disk housing shell portion of the catheter handle of FIG. 2.
Figure 4:
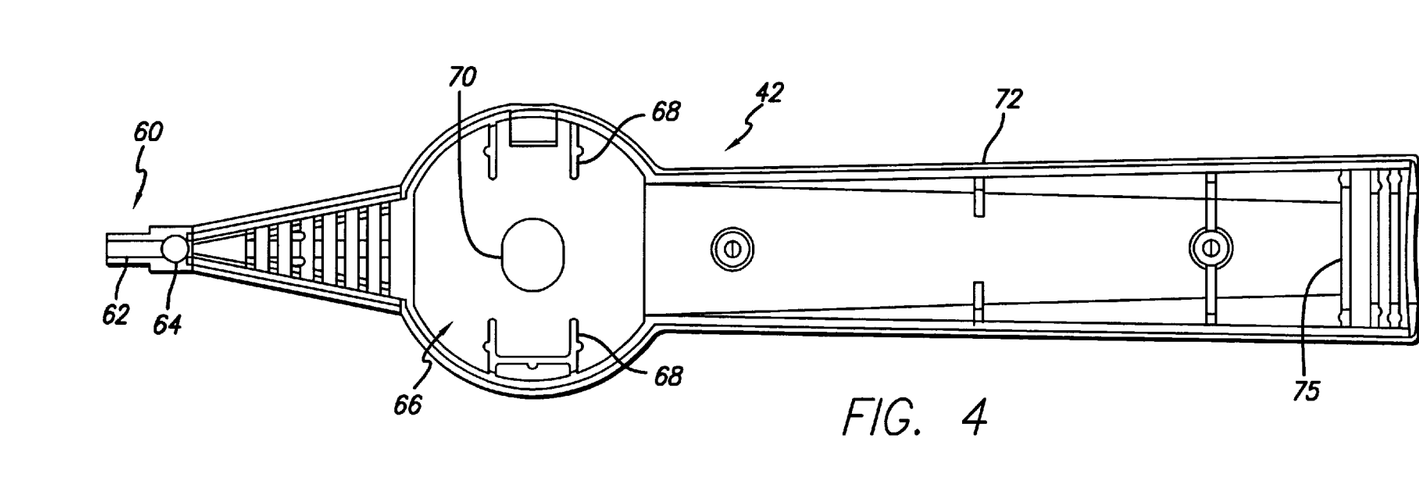
FIG. 4 is plan view depicting the spacer housing shell portion of the catheter handle of FIG. 2.

The shell 34 of the handle 10 comprises a disk housing shell 40 (FIG. 3) and a spacer housing shell 42 (FIG. 4). Referring to FIG. 3 which depicts the internal configuration of the disk housing shell 40, the distal end 44 of the disk housing shell includes a channel 46 for receiving and housing the catheter shaft 14 (FIG. 2). Proximal the channel 46 is a pocket 48 that receives a cylindrical adapter (not shown in FIG. 3). As will be discussed in more detail below, the catheter shaft 14 is adhesively bonded into a hole in the adapter, and the adapter is adhesively bonded into the pocket 48, thus holding the catheter shaft in place relative to the handle 10. Proximal the pocket 48 is a steering disk housing 50. One side along the inner perimeter of the steering disk housing 50 includes a plurality of alternating protrusions and recesses 52. As will be discussed further below, the alternating protrusions and recesses 52 in the steering disk housing 50 mate with a plurality of alternating protrusions and recesses on a steering disk (not shown in FIG. 3). The steering disk housing 50 also includes a lateral slot 54 that receives and controls the direction of translation of a steering controller shaft (not shown in FIG. 3). Proximal the steering disk housing 50 is a hand-grip portion 56 of the disk housing shell 40. The proximal-most portion of the hand-grip portion 56 includes a channel 58 for holding an electrical connector 59 (FIG. 5).

Referring to FIG. 4 which depicts the internal configuration of the spacer housing shell 42, the distal end 60 of the spacer housing shell includes a channel 62 for receiving and housing the catheter shaft 14 (FIG. 2). Proximal the channel 62 is a pocket 64 that receives a cylindrical adapter (not shown in FIG. 4). Upon assembly (not shown) of the handle shell 34, the channel 62 complements the channel 46 in the disk housing shell 40 (FIG. 3) to form a lumen to house the proximal portion 12 of the catheter shaft 14 (FIG. 2), and the pocket 64 complements the pocket 48 (FIG. 3) in the disk housing shell to form a single pocket for housing the cylindrical adapter. Proximal the pocket 64 is a spacer housing 66. Within the spacer housing 66 is a rectangular pocket 68 for containing a spacer (not shown in FIG. 4); the spacer will be described in more detail below. The rectangular pocket 68 permits the spacer to translate laterally, but restrains the spacer from translating longitudinally. The spacer housing 66 also includes a lateral slot 70 that is aligned with the lateral slot 54 (FIG. 3) in the steering disk housing 50 to receive and control the direction of translation of the steering controller shaft (not shown in FIG. 4). Proximal the spacer housing 66 is a hand-grip portion 72 of the spacer housing shell 42. The hand-grip portion 72 of the spacer housing shell 42 mates with the hand-grip portion 56 (FIG. 3) of the disk housing shell 40 to form a complete hand-grip 74 (see FIG. 2). The proximal-most portion of the hand-grip portion 72 includes a channel 75 that complements the channel 58 (FIG. 3) in the disk housing shell 40 to form an aperture for holding an electric connector 59 (FIG. 5).

Figure 5:
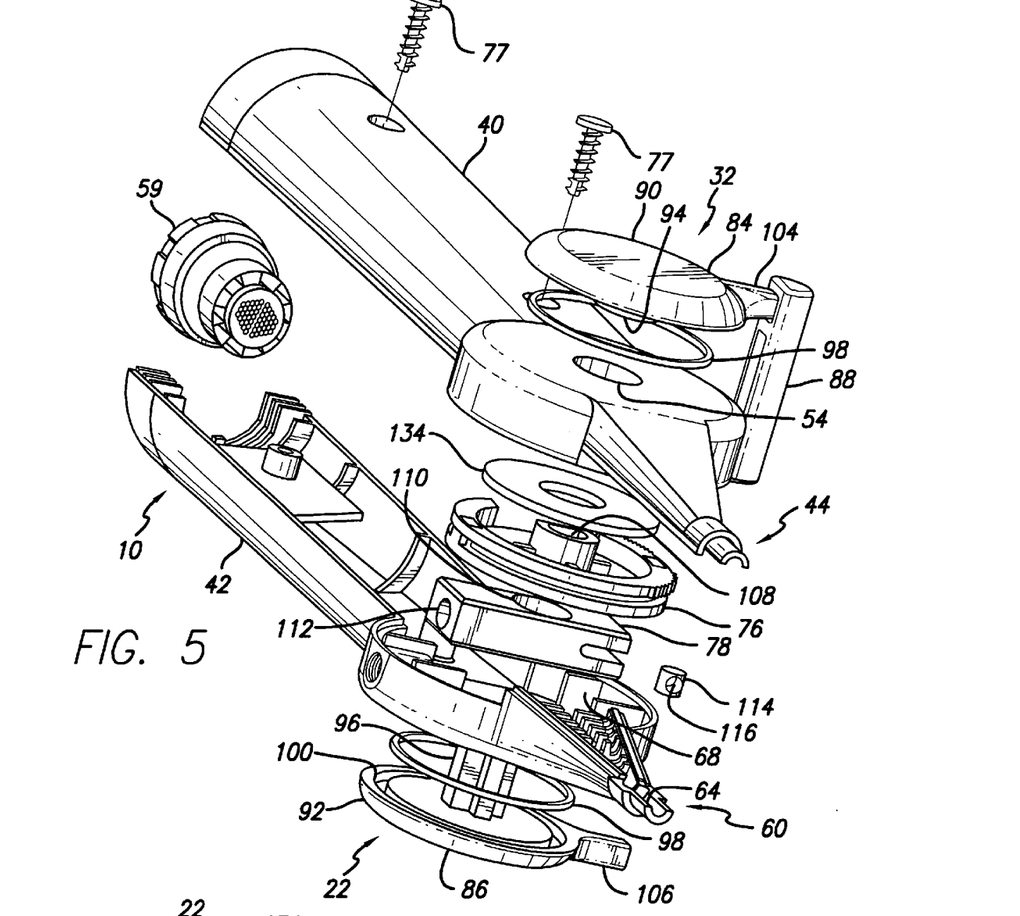
FIG. 5 is an exploded isometric view of the handle of FIG. 2 depicting major components of the catheter handle including the handle shell and the steering controller.

With reference to FIG. 5, the disk housing shell 40 and spacer housing shell 42 are mated and joined to each other at various attachment points after installation of the interior components of the handle. One of the attachment points is at the location of the cylindrical-shape adapter 114. The adapter 114 fits into the matching pockets 48 (FIG. 3), 64 (FIG. 4) within the distal section 44, 60 of the disk housing shell 40 and the spacer housing shell 42 respectively. The adapter 114 is adhesively bonded to the matching pockets 48 (FIG. 2), 64 (FIG. 3), such as with cyanoacrylate adhesive, thereby joining the disk housing shell 40 and the spacer housing shell 42 at that attachment point. The disk housing shell 40 and the spacer housing shell 42 are also joined at at least one other attachment point with a screw 77. In the embodiment of FIG. 5, two screws 77 are shown.

Figure 6:
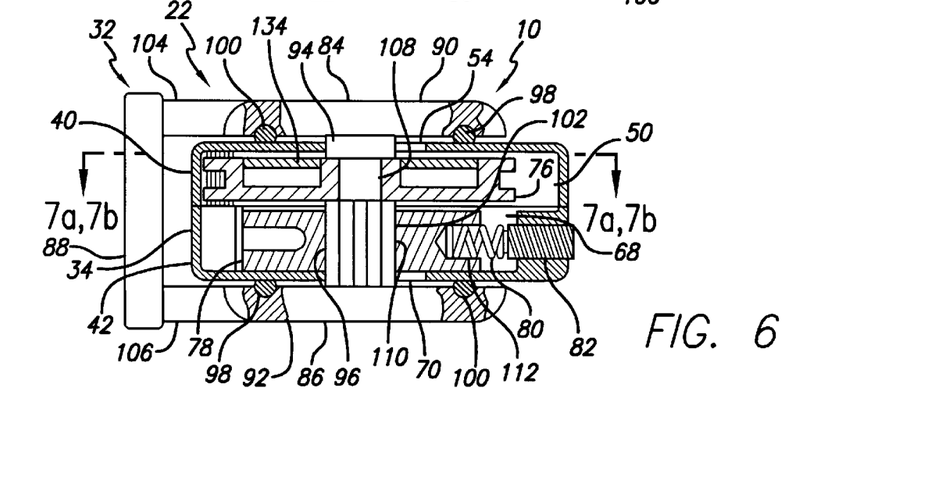
FIG. 6 is a section view of the steering controller taken along the line 6—6 from FIG. 2.

With further reference to FIG. 5 and reference to FIG. 6, the steering controller 22 comprises the knob 32, a steering disk 76, a spacer 78, a compression spring 80, and a setscrew 82. The knob 32 further comprises a knob disk hub 84, a knob disk shaft 86, and a knob connecting bar 88. The knob disk hub 84 and the knob disk shaft 86 each comprise a disk portion 90, 92 and a shaft portion 94, 96. The shaft portions 94, 96 protrude perpendicularly from the center of their respective disk portions 90, 92. The shaft portion 94 of the knob disk hub 84 is inserted into the lateral slot 54 in the disk housing shell 40 and the shaft portion 96 of the knob disk shaft 86 is inserted into the lateral slot 70 in the spacer housing shell 42. O-rings 98 are placed within grooves 100 in the knob disk hub 84 and the knob disk shaft 86 to provide standoff between the steering knob 32 and the handle shell 34 so that the steering knob does not rub against the handle shell. Both O-rings 98 are lubricated with silicone oil, such as Dow™ 360 or equivalent, to minimize drag. Within the handle 10, the shaft portion 94 of the knob disk hub 84 mates with and is adhesively bonded, such as by gluing, to the shaft portion 96 of the knob disk shaft 86, thus forming a single shaft 102. The knob connecting bar 88 is also adhesively bonded, such as by gluing, between radial protrusions 104, 106 on the knob disk hub 84 and the knob disk shaft 86 to ensure that the knob disk hub and the knob disk shaft move synchronously.

With continued reference to FIGS. 5 and 6, a center hole 108 on the steering disk 76 is keyed to the shaft portion 102 of the knob 32 so that turning the knob causes the steering disk to rotate. The spacer 78 also has a hole 110 that mates with the shaft 102 of the knob 32. The hole 110 in the spacer 78 is round and provides a loose fit with the shaft 102. The spacer 78 is a mostly rectangular-shape block that fits within the rectangular pocket 68 in the spacer housing shell 42. The spacer 78 is normally biased to one side of the pocket by the compression spring 80. The compression spring 80 fits between the setscrew 82 within the wall of the spacer housing shell 42 and an aperture 112 in an end of the spacer 78. The force exerted by the compression spring 80 can be adjusted via the setscrew 82.

Although in a preferred embodiment the spacer 78 is biased by a compression spring 80, other means may be utilized to accomplish the same result. For instance, the spacer 78 can be biased by tension springs, leaf springs, or numerous other types of springs. The spacer 78 can also be biased by hydraulic pressure, pneumatic pressure, compressible materials, elastic materials, magnetic forces, or by any equivalent means. Similarly, the force exerted by the compression spring 80 can be adjusted by means other than a setscrew 82 to accomplish the same result. As an example, other types of screws or threaded devices could be used. The force can also be adjusted by a ratchet system, shims, wedges, hydraulic pressure, pneumatic pressure, or by any equivalent means.

Figure 7A:
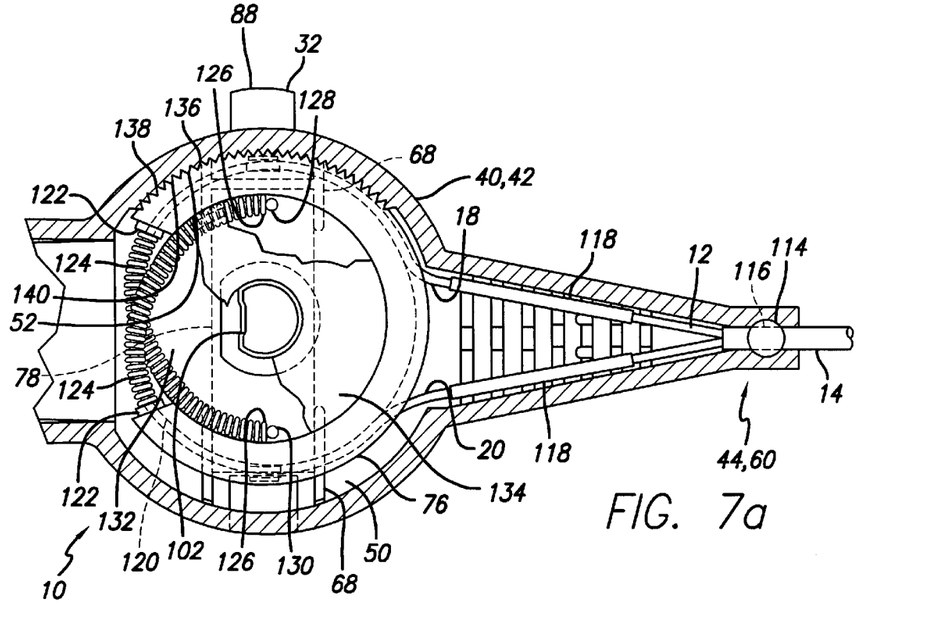
FIG. 7a is a section view of the steering controller taken along line 7a—7a in FIG. 6 depicting the steering controller engaged with the handle shell in the locked-position.
Figure 7B:
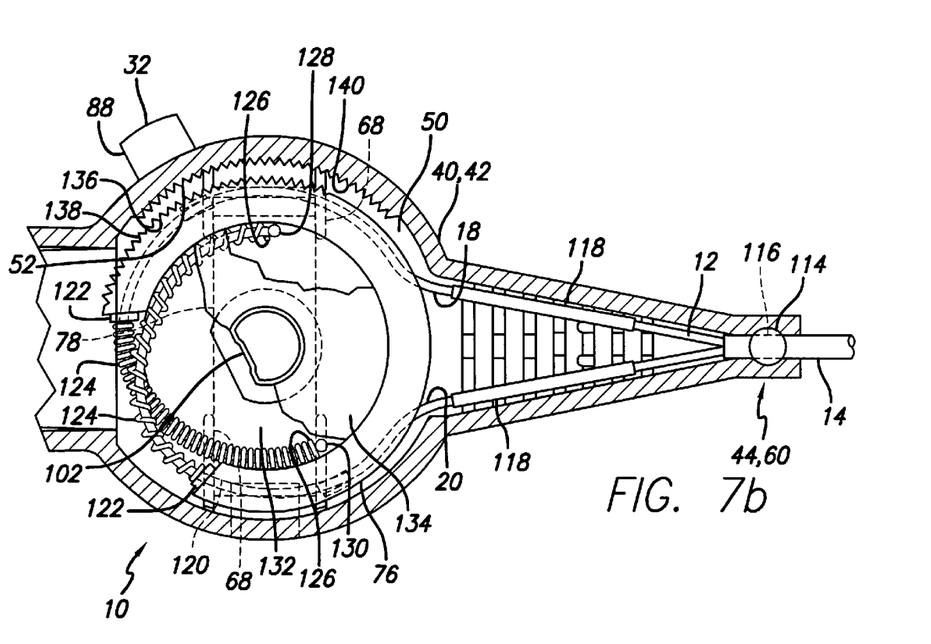
FIG. 7b is a section view of the steering controller taken along line 7b—7b in FIG. 6 depicting the steering controller disengaged from the handle shell in the free-position and rotated in a first direction.

Referring to FIGS. 7a and 7b, a cylindrical-shape adapter 114 with a hole 116 (see FIG. 5) running laterally through it fits into the matching pockets 48 (FIG. 3), 64 (FIG. 4) within the distal section 44, 60 of the spacer housing shell 42 and the disk housing shell 40. To attach the catheter shaft 14 to the handle 10, the proximal end 12 of the catheter shaft is inserted into the hole 116 and is attached to the hole such as by adhesive bonding. As previously mentioned, the adapter 114 is subsequently attached to the matching pockets 48 (FIG. 3), 64 (FIG. 4), such as by adhesive bonding.

With continued reference to FIGS. 7a and 7b, the first 18 and second 20 steering tendons exit the proximal end 12 of the catheter shaft 14 and enter the handle 10. Within the handle 10, the steering tendons 18, 20 are routed through guide tubes 118 that comprise a low-friction material, such as polyimide. From the guide tubes 118, each of the steering tendons 18, 20 wraps partially around a hub 120 of the steering disk 76 and feeds through a tendon stop 122 that is secured to the steering disk, and a compression spring 124. A proximal end 126 of each of the compression springs 124 is preferably attached to the proximal end 128, 130 of each of the steering tendons 18, 20, such as by soldering. The soldered ends of the compression springs 124 and steering tendons 18, 20 are then routed within a cavity 132 in the steering disk 76. A cover 134 is then attached, such as by gluing, to the hub 120 of the steering disk 76 in order to capture the compression springs 124 within the cavity 132, thereby preventing the proximal ends of the steering tendons 18, 20 and the compression springs 124 from interfering with other components within the handle 10. In an alternate embodiment (not shown), a tendon stop is attached to the proximal ends of each steering tendon and the compression springs are located between the tendon stops and the tendon exit points on the steering disk 76.

Figure 8A:
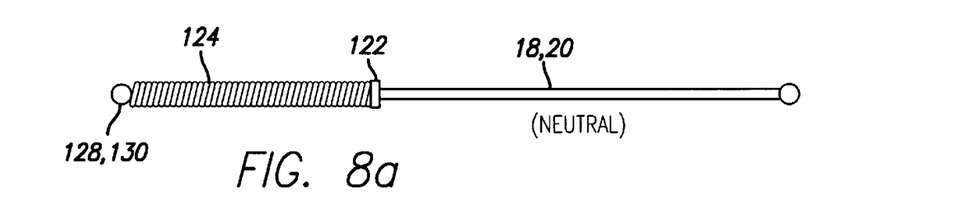
FIGS. 8a–8c are schematic diagrams of the catheter steering system of the catheter of FIG. 2 having a steering tendon passing through a stop and a compression spring, showing the tendon and the spring with the tendon in a neutral (non-steered) position, a tensed (steered) state and a relaxed (non-steered) state.
Figure 8B:
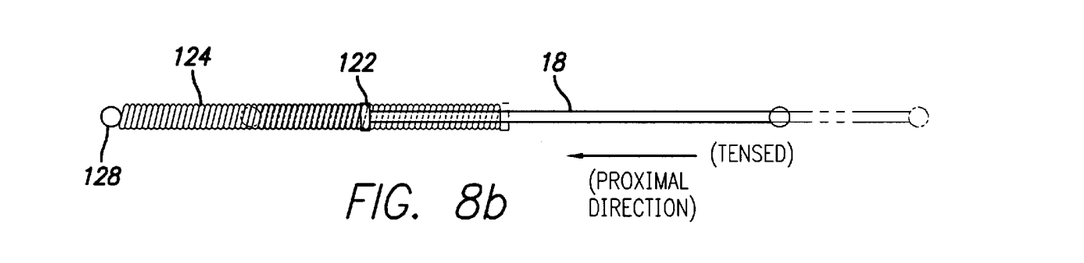
Figure 8C:
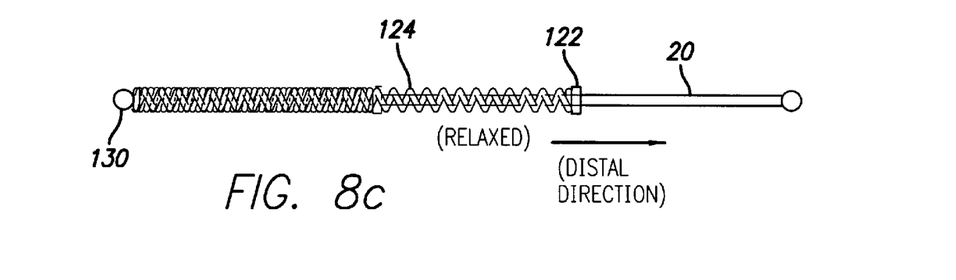

Turning now to FIGS. 8a through 8b, in one configuration, when the steering disk 76 is in the neutral steering position, both compression springs 124 are fully compressed (see FIG. 8a) between their proximal ends 126 and their tendon stops 122 and provide continuous tension on the first 18 and second 20 steering tendons. Although only one tendon and spring are shown in FIG. 8a, both are indicated by numerals because both have the same configuration. Since the compression springs 124 are fully compressed when the steering disk 76 is in the neutral position, rotation of the steering disk in a first direction relative the neutral position causes the tendon stop 122 to push on the compression spring attached to the first steering tendon 18 and to immediately translate the first steering tendon in the proximal direction with the compression spring on the first steering tendon remaining fully compressed as shown in FIG. 8b. As also shown in FIG. 8b, the distal end of the first steering tendon 18 also translates to the left of the figure (proximal direction) along with movement of the compressed spring 124. Its attachment to the distal end of the catheter (shown) causes deflection of the catheter shaft 14. The compression spring 124 on the second steering tendon 20, however, increases in length, yet remains partially compressed, and thereby provides continuous tension on the second steering tendon (see FIG. 8c). As the steering disk 76 is rotated in the first direction, the axial translation of the first steering tendon 18 in the proximal direction causes the catheter shaft 14 to steer. Conversely, rotation of the steering disk 76 in a second direction relative the neutral position causes the tendon stop 122 to push on the compression spring 124 attached to the second steering tendon 20 and to immediately translate the second steering tendon in the proximal direction with the compression spring on the second steering tendon remaining fully compressed. The compression spring 124 on the first steering tendon 18, however, increases in length, yet remains partially compressed, and thereby provides continuous tension on the first steering tendon.

In another configuration, when the steering disk 76 is in the neutral steering position, both compression springs 124 are partially compressed (see FIG. 8a) and provide continuous tension on the first 18 and second 20 steering tendons. Since the compression springs 124 are only partially compressed when the steering disk 76 is in the neutral position, rotation of the steering disk in a first direction relative the neutral position causes the tendon stop 122 to compress the spring attached to the first steering tendon 18 further, thus providing some play prior to translating the first steering tendon in the proximal direction. The compression spring 124 on the second steering tendon 20, however, remains partially compressed while increasing in length and thereby provides continuous tension on the second steering tendon (see FIG. 8c). Conversely, rotation of the steering disk 76 in a second direction relative the neutral position causes the tendon stop 122 to compress the compression spring 124 attached to the second steering tendon further 20, thus providing some play prior to translating the second steering tendon in the proximal direction. The compression spring 124 on the first steering tendon 18, however, remains partially compressed while increasing in length and thereby provides continuous tension on the first steering tendon. Although a catheter with two steering tendons with a compression springs to maintain tension on the tendons is disclosed, the compression springs of the present invention can be incorporated into catheters having only one steering tendon or more than two steering tendons.

In a preferred embodiment, the steering tendons 18, 20 are continuously maintained in tension through the use of compression springs 124 (see FIGS. 8a–8c), however, other means may be utilized to accomplish the same result. For instance, the steering tendons 18, 20 can be continuously maintained in tension by tension springs, leaf springs, or numerous other types of springs. The steering tendons 18, 20 can also be continuously maintained in tension by hydraulic pressure, pneumatic pressure, compressible materials, elastic materials, or by any equivalent means. Similarly, although a preferred embodiment utilizes the compression spring 124 in combination with a steering disk 76 as a steering device, means other than a steering disk can be used to cause axial translation of the steering tendons 18, 20. For example, the steering tendon tensioning means can be used in combination with other tendon steering devices such as wheels, cams, wedges, levers, pistons, sliding devices, threaded devices, geared devices, or any equivalent steering means.

If the biasing forces of the compression springs 124 are too strong, they will cause an undesirable condition. The overly strong springs will translate the steering tendons 18, 20 in the proximal direction and cause the distal-end region of the catheter sheath to deflect independently of manipulation of the steering controller 22. Therefore, the biasing force exerted by the compression springs 124 against their respective tendons 18, 20 must be sufficient to maintain the steering tendons in continuous tension while at the same time being less than the amount of force necessary to deflect the distal end of the catheter shaft 14. That is, the compression springs 124 must have a negligible impact on the profile of the catheter shaft 14. The amount of force exerted by the spring varies continuously as it extends or contracts (according to the linear formula $F=k(X)$, wherein "F" is force, "k" is a constant spring rate that depends on a combination of spring geometry and material, and "X" is the distance of extension or compression). In one configuration, the compression spring 124 has a free length of about 50 mm (two inches) and a fully compressed length of about 25 mm (one inch), resulting in a 25 mm range of travel. Also in this configuration, the compression spring 124 has a spring rate of about 68 grams (2.4 ounces) per 25 mm, meaning that it will take about 68 grams of force to compress the spring 25 mm. Although a compression spring with a free length of about 50 mm, a fully compressed length of about 25 mm, and a spring rate of about 68 grams is disclosed, springs having longer or shorter lengths and requiring higher or lower amounts of force to fully compress the spring may also be used successfully. However, the spring rate, free length, and fully compressed length of the compression spring should be sufficient to ensure that continuous tension will be maintained on the steering tendon while at the same time imposing negligible impact on the profile of the catheter shaft.

With further reference to FIGS. 7a and 7b, a perimeter of the steering disk 76 includes a plurality of alternating protrusions and recesses 136 that mate with the plurality of alternating protrusions and recesses 52 on the inside surface of the steering disk housing 50 (FIG. 7a). The resolution of locking locations is controlled by the sizes and spacing of the protrusions and recesses 52, 136. The number of locking positions increases as the number of protrusions and recesses 52, 136 increases. The finer the protrusions and recesses 52, 136 are, the more that can be disposed in any given arc. This allows greater resolution. However, they cannot be so fine that a force on the distal end of the catheter translated to the steering controller 22 by a tendon 18, 20 can pull the steering disk 76 out of its locked position. In one configuration, the alternating protrusions and recesses 136 on the steering disk 76 and the alternating protrusions and recesses 52 in the steering disk housing 50 are teeth 138, 140. The teeth 138 on the steering disk 76 can be disengaged (FIG. 7b) from the teeth 140 in the steering disk housing 50 by pushing the knob connecting bar 88 radially towards the center of the handle 10 with a force greater than the biasing force of the spring 80 (FIG. 6). More specifically, by pushing the knob connecting bar 88 radially towards the center of the handle 10 with a force greater than the biasing force of the spring 80 (FIG. 6), the shaft 102 translates within the slots 54, 70 (FIG. 6) in the spacer housing 66 (FIG. 4) and the steering disk housing 50. As the steering knob 32 translates, the shaft 102 causes the steering disk 76 and the spacer 78 to translate with it, thereby causing the teeth 138 in the steering disk to disengage from the steering disk housing 50 and causing further compression of the compression spring 80 (FIG. 6). With the steering disk 76 disengaged (FIG. 7b), the knob connecting bar 88 can be rotated clockwise or counterclockwise about the shaft 102, thus rotating the steering disk and pulling one of the steering tendons 18, 20 to cause the profile of the distal-end region 24 (FIG. 2) of the catheter shaft 14 to change.

Although in a preferred embodiment the steering disk 76 mates with the steering disk housing 50 through a plurality of alternating protrusions and recesses 136, 52 on the steering disk and on the steering disk housing, other means may be utilized to accomplish the same result. For instance, an array of protrusions can be disposed on the steering disk 76 for mating with an array of recesses disposed on the steering disk housing 50, or vice versa. Alternatively, the same result can be achieved with a single protrusion on the steering disk 76 that mates with any of a series of recesses on the steering disk housing 50, or vice versa, or by any equivalent means.

With additional reference to FIGS. 7a and 7b, when the desired profile 36, 38 (FIG. 2) of the distal-end region 24 of the catheter shaft 14 has been reached, the applied force on the knob connecting bar 88 is reduced to an amount less than the biasing force of the compression spring 80 (FIG. 6). Reducing the applied force on the knob connecting bar 88 allows the compression spring 80 (FIG. 6) to decompress and biases the spacer 78 back to the opposite side of the rectangular pocket 68 (FIG. 6). As the compression spring 80 (FIG. 6) biases the spacer 78, the spacer causes the shaft 102 to translate with it, which in turn causes the steering disk 76 to translate and to reengage with the teeth 140 in the steering disk housing 50. With the force removed from the knob connecting bar 88 and the compression spring 80 (FIG. 6) biasing the spacer 78, the steering disk 76 is locked in place and maintains the changed profile 36, 38 (FIG. 2) of the distal-end region 24 of the catheter shaft 14. Thus, because of its ability to automatically hold the catheter's distal profile 36, 38 (FIG. 2) when released, the handle 10 does not require a second operation to lock the desired profile in place.

In operation, the set of teeth 138 on the steering disk 76 is normally interrelated with the set of teeth 140 on the inside surface of the steering disk housing 50. To change the profile of the distal-end region 24 (FIG. 2) of the catheter shaft 14 and lock it in place, the operator first disengages the teeth 138 on the steering disk 76 from the teeth 140 on the inside surface of the steering disk housing 50 (see FIGS. 7a and 7b). This step is accomplished by the operator applying a force to the knob connection bar 88 of the steering controller 22 that is greater than the biasing force of the compression spring 80 (FIG. 6). With the teeth 138 (FIG. 7b) on the steering disk 76 disengaged from the teeth 140 on the inside surface of the steering disk housing 50, the operator can rotate the controller 22 to affect the profile of the distal-end region 24 of the shaft 14 (FIG. 2). Upon obtaining a desired profile 36, 38 (FIG. 2) of the distal-end region 24 of the shaft 14, the teeth 138 (FIG. 7a) on the steering disk 76 are reengaged with the teeth 140 on the inside surface of the steering disk housing 50 by the operator applying a force less than the biasing force of the compression spring 80 (FIG. 6) to the steering controller 22.

It will be apparent from the foregoing that, while particular forms of the invention have been illustrated and described, various modifications can be made without departing from the spirit and scope of the invention.

What is claimed is:

1. A system for applying tension to a steering tendon, the tendon having a distal end attached to the distal-end region of a catheter shaft and a proximal end exiting the proximal end of the shaft, said system comprising:

a rotatable steering controller;

a stop disposed at the controller having the proximal end of the tendon passing therethrough and terminating at a point a distance from the stop; and a spring device having a distal end at the stop and a proximal end attached to the tendon at a location proximal to the stop;

wherein movement of the controller in a first direction relative a neutral position increases tension on the tendon and movement of the controller in a second direction relative the neutral position and opposite the first direction, maintains tension on the tendon.

2. The system of claim 1 wherein the spring device is in a fully compressed state when the steering controller is in the neutral position and when the steering controller is moved in the first direction.

3. The system of claim 1 wherein:

the spring device is in a partially compressed state when the steering controller is in the neutral position; and the compression increases when the steering controller is moved in the first direction.

4. The system of claim 1 wherein the spring device extends in length when the steering controller is moved in the second direction, yet remains in compression.

5. The system of claim 1 wherein the spring device comprises a wire coil surrounding the tendon between the stop and the proximal end of the tendon.

6. The system of claim 1 wherein the catheter shaft has an inherent bending stiffness and the tension imparted by the spring device when the controller is in the neutral position has a negligible impact on the profile of the catheter shaft.

7. A system for applying tension to a first steering tendon and a second steering tendon, each tendon having a distal end attached to the distal-end region of a catheter shaft and a proximal end exiting the proximal end of the shaft, said system comprising:

a rotatable steering controller;

a first stop disposed at the controller and having the proximal end of the first tendon passing therethrough and terminating at a point distant from the first stop;

a first spring device having a distal end at the first stop and a proximal end attached to the proximal end of the first tendon;

a second stop disposed at the controller and having the proximal end of the second tendon passing therethrough and terminating at a point a distance from the second stop; and a second spring device having a distal end at the second stop and a proximal end attached to the proximal end of the second tendon;

wherein movement of the controller in a first direction relative a neutral position increases tension on the first tendon while maintaining tension on the second tendon and movement of the controller in a second direction relative the neutral position increases tension on the second tendon while maintaining tension on the first tendon.

8. The system of claim 7 wherein the first and second spring devices are in a compressed state when the steering controller is in the neutral position and thereby maintain tension on the first and second tendons respectively.

9. The system of claim 8 wherein the catheter shaft has an inherent bending stiffness and the tension imparted by the first and second spring devices when the controller is in the neutral position has negligible impact on the profile of the catheter shaft.

10. The system of claim 8 wherein:

the first spring device is in a fully compressed state and the second spring device has extended, yet remains in a compressed state when the controller is moved in the first direction; and the second spring device is in a fully compressed state and the first spring device has extended, yet remains in a compressed state when the controller is moved in the second direction.

11. The system of claim 7 wherein:

the first and second spring devices are in a partially compressed state when the steering controller is in the neutral position;

the compression increases on the first spring device when the steering controller is moved in a first direction; and the compression increases on the second spring device when the steering controller is moved in a second direction.

12. The system of claim 11 wherein the catheter shaft has an inherent bending stiffness and the tension imparted by the first and second spring devices when the controller is in the neutral position has negligible impact on the profile of the catheter shaft.

13. A system for applying tension to a steering tendon, the tendon having a distal end attached to the distal-end region of a catheter shaft and a proximal end exiting the proximal end of the shaft, said system comprising:

a rotatable steering controller having the proximal end of the tendon passing therethrough and terminating at a point a distance from the steering controller; and a spring device having a distal end positioned proximate the tendon exit paint of the steering controller and a proximal end attached to the tendon at a location proximal to the steering controller;

wherein movement of the steering controller in a first direction relative a neutral position increases tension on the tendon and movement of the steering controller in a second direction relative the neutral position and opposite the first direction, maintains tension on the tendon.

14. A system for applying tension to a steering tendon, the tendon having a distal end attached to the distal-end region of a catheter shaft and a proximal end exiting the proximal end of the shaft, said system comprising:

a rotatable steering controller having a cavity;

a stop disposed at the controller having the proximal end of the tendon passing therethrough and terminating at a point a distance from the stop; and a spring device having a distal end at the stop and a proximal end attached to the tendon at a location proximal to the stop;

wherein the proximal end of the spring and the proximal end of the tendon are positioned within the cavity of the controller; and wherein movement of the controller in a first direction relative a neutral position increases tension on the tendon and movement of the controller in a second direction relative the neutral position and opposite the first direction, maintains tension on the tendon, the proximal end of the spring and the proximal end of the tendon remaining in the cavity of the controller during movement of the controller.

15. The system of claim 14 wherein the spring device is in a fully compressed state when the steering controller is in the neutral position and when the steering controller is moved in the first direction.

16. The system of claim 14, wherein:

the spring device is in a partially compressed state when the steering controller is in the neutral position; and the compression increases when the steering controller is moved in the first direction.

17. The system of claim 14, wherein the spring device extends in length when the steering controller is moved in the second direction, yet remains in compression.

18. The system of claim 14, wherein the spring device comprises a wire coil surrounding the tendon between the stop and the proximal end of the tendon.

19. The system of claim 14, wherein the catheter shaft has an inherent bending stiffness and the tension imparted by the spring device when the controller is in the neutral position has a negligible impact on the profile of the catheter shaft.

20. A system for applying tension to a first steering tendon and a second steering tendon, each tendon having a distal end attached to the distal-end region of a catheter shaft and a proximal end exiting the proximal end of the shaft, said system comprising:

a rotatable steering controller having a cavity;

a first stop disposed at the controller and having the proximal end of the first tendon passing therethrough and terminating at a point a distance from the first stop;

a first spring device having a distal end at the first stop and a proximal end attached to the proximal end of the first tendon;

a second stop disposed at the controller and having the proximal end of the second tendon passing therethrough and terminating at a point a distance from the second stop; and a second spring device having a distal end at the second stop and a proximal end attached to the proximal end of the second tendon;

wherein the proximal end of the first spring device and the proximal end of the first tendon are positioned within the cavity of the controller;

wherein the proximal end of the second spring device and the proximal end of the second tendon are positioned within the cavity of the controller; and wherein movement of the controller in a first direction relative a neutral position increases tension on the first tendon while maintaining tension on the second tendon and movement of the controller in a second direction relative the neutral position increases tension on the second tendon while maintaining tension on the first tendon the proximal end of the first and second spring device and the proximal end of the first and second tendon remaining in the cavity of the controller during movement of the controller.

21. The system of claim 20, wherein the first and second spring devices are in a compressed state when the steering controller is in the neutral position and thereby maintain tension on the first and second tendons respectively.

22. The system of claim 21, wherein the catheter shaft has an inherent bending stiffness and the tension imparted by the first and second spring devices when the controller is in the neutral position has negligible impact on the profile of the catheter shaft.

23. The system of claim 21, wherein:

the first spring device is in a fully compressed state and the second spring device has extended, yet remains in a compressed state when the controller is moved in the first direction; and the second spring device is in a fully compressed state and the first spring device has extended, yet remains in a compressed state when the controller is moved in the second direction.

24. The system of claim 20, wherein:

the first and second spring devices are in a partially compressed state when the steering controller is in the neutral position;

the compression increases on the first spring device when the steering controller is moved in a first direction; and the compression increases on the second spring device when the steering controller is moved in a second direction.

25. The system of claim 24, wherein the catheter shaft has an inherent bending stiffness and the tension imparted by the first and second spring devices when the controller is in the neutral position has negligible impact on the profile of the catheter shaft.

* * * * *